(12) United States Patent
Van Bavel et al.

(10) Patent No.: US 9,999,873 B2
(45) Date of Patent: Jun. 19, 2018

(54) PROCESS FOR PREPARING A CHLORINE COMPRISING CATALYST, THE PREPARED CATALYST, AND ITS USE

(71) Applicant: SHELL OIL COMPANY, Houston, TX (US)

(72) Inventors: Alexander Petrus Van Bavel, Amsterdam (NL); Gerrit Leendert Bezemer, Amsterdam (NL); Peter John Van Den Brink, Amsterdam (NL); Erwin Roderick Stobbe, Amsterdam (NL)

(73) Assignee: SHELL OIL COMPANY, Houston, TX (US)

( * ) Notice: Subject to any disclaimer, the term of this patent is extended or adjusted under 35 U.S.C. 154(b) by 0 days. days.

(21) Appl. No.: 15/643,051

(22) Filed: Jul. 6, 2017

(65) Prior Publication Data

US 2017/0297006 A1    Oct. 19, 2017

Related U.S. Application Data (63) Continuation of application No. 14/906,911, filed as application No. PCT/EP2014/065058 on Jul. 14, 2014, now Pat. No. 9,737,882.

(30) Foreign Application Priority Data

Jul. 24, 2013   (EP) .................................... 13177879

(51) Int. Cl.
*B01J 27/13*     (2006.01)
*B01J 27/135*    (2006.01)
(Continued)

(52) U.S. Cl.
CPC ............. *B01J 27/135* (2013.01); *B01J 27/10* (2013.01); *B01J 27/138* (2013.01);
(Continued)

(58) Field of Classification Search
CPC . B01J 27/135; B01J 27/10; B01J 27/13; B01J 27/138; B01J 37/0009;
(Continued)

(56) References Cited

U.S. PATENT DOCUMENTS 2,768,961 A   10/1956  Weck et al.
3,134,732 A   5/1964   Kearby et al.
(Continued)

FOREIGN PATENT DOCUMENTS

CN    1083415 A    3/1994
CN    1785515 A    6/2006
(Continued)

OTHER PUBLICATIONS

Rosynek et al., "Effect of cobalt source on the reduction properties of silica-supported cobalt catalysts", Applied Catalysis, vol. 73, 1991, pp. 97-112.
(Continued)

*Primary Examiner* — Patricia L. Hailey (57) ABSTRACT

The invention concerns a process for preparing a chlorine comprising catalyst by (a) providing a Fischer-Tropsch catalyst comprising titania and at least 5 weight percent cobalt; (b) impregnating the catalyst with a solution comprising chloride ions; and (c) heating the impregnated catalyst at a temperature in the range of between 100 and 500° C. for at least 5 minutes up to 2 days. The prepared catalyst preferably comprises 0.13-3 weight percent of the element chlorine. The invention further relates to the prepared catalyst and its use.

8 Claims, 7 Drawing Sheets

(51) Int. Cl.

| | | |
|---|---|---|
| *B01J 37/04* | (2006.01) | |
| *B01J 37/08* | (2006.01) | |
| *B01J 37/24* | (2006.01) | |
| *B01J 27/10* | (2006.01) | |
| *B01J 27/138* | (2006.01) | |
| *B01J 37/00* | (2006.01) | |
| *C07C 1/04* | (2006.01) | |
| *C10G 2/00* | (2006.01) | |
| *B01J 37/02* | (2006.01) | |
| *C07C 11/10* | (2006.01) | |
| *B01J 23/889* | (2006.01) | |
| *B01J 35/02* | (2006.01) | |

(52) U.S. Cl.
CPC ....... *B01J 37/0009* (2013.01); *B01J 37/0201* (2013.01); *B01J 37/04* (2013.01); *B01J 37/08* (2013.01); *B01J 37/24* (2013.01); *C07C 1/0435* (2013.01); *C07C 11/10* (2013.01); *C10G 2/332* (2013.01); *B01J 23/8892* (2013.01); *B01J 23/8896* (2013.01); *B01J 35/023* (2013.01); *C07C 2521/06* (2013.01); *C07C 2523/34* (2013.01); *C07C 2523/75* (2013.01); *C07C 2523/889* (2013.01)

(58) Field of Classification Search
CPC ........ B01J 37/0201; B01J 37/04; B01J 37/08; B01J 37/24; B01J 23/8892; B01J 23/8896; B01J 35/023; C07C 1/0435; C07C 11/10; C07C 2521/06; C07C 2523/34; C07C 2523/75; C07C 2523/889; C10G 2/332
USPC ........ 502/224, 227, 229, 230; 518/715, 720, 518/721, 728
See application file for complete search history.

(56) References Cited

U.S. PATENT DOCUMENTS

| | | | |
|---|---|---|---|
| 3,842,121 A | 10/1974 | Ichikawa et al. | |
| 3,888,789 A | 6/1975 | Dombro et al. | |
| 4,136,127 A | 1/1979 | Antos | |
| 4,568,663 A | 2/1986 | Mauldin | |
| 4,585,798 A | 4/1986 | Beuther et al. | |
| 4,595,703 A | 6/1986 | Payne et al. | |
| 4,728,672 A * | 3/1988 | Yoshinari | B01J 27/045 518/713 |
| 5,102,851 A | 4/1992 | Eri et al. | |
| 6,087,405 A | 7/2000 | Plecha et al. | |
| 6,262,132 B1 * | 7/2001 | Singleton | B01J 21/04 502/303 |
| 6,759,440 B2 | 7/2004 | Geerlings et al. | |
| 7,585,808 B2 * | 9/2009 | Malek | B01J 20/02 502/20 |
| 2006/0166809 A1 | 7/2006 | Malek et al. | |
| 2007/0123594 A1 | 5/2007 | Dogterom et al. | |
| 2010/0048742 A1 | 2/2010 | Ellis et al. | |
| 2016/0175820 A1 | 6/2016 | Bezemer et al. | |
| 2016/0175821 A1 * | 6/2016 | Van Bavel | B01J 27/138 518/715 |

FOREIGN PATENT DOCUMENTS

| | | |
|---|---|---|
| EP | 2301663 A1 | 3/2011 |
| WO | 8601500 A1 | 3/1986 |
| WO | 9700231 A1 | 1/1997 |
| WO | 9934917 A1 | 7/1999 |
| WO | 03018481 A1 | 3/2003 |
| WO | 2005030680 A1 | 4/2005 |
| WO | 2008071640 A2 | 6/2008 |

OTHER PUBLICATIONS

Bae et al., "Effect of support and cobalt precursors on the activity of Co/AlPO4 catalysts in Fischer-Tropsch synthesis", Journal of Molecular Catalysis A: Chemical, vol. 311, 2009, pp. 7-16.

Feltes et al., "Selective adsorption of manganese onto cobalt for optimized Mn/Co/TiO2 Fischer-Tropsch catalysts", Journal of Catalysis, vol. 270, No. 1, Mar. 22, 2010, pp. 95-102.

* cited by examiner

PROCESS FOR PREPARING A CHLORINE COMPRISING CATALYST, THE PREPARED CATALYST, AND ITS USE

CROSS-REFERENCE TO RELATED APPLICATIONS

The present application is a Continuation Application claiming benefit of U.S. application Ser. No. 14/906,911, filed Jan. 22, 2016, which is a National Stage (§ 371) Application of International Application No. PCT/EP2014/065058, filed Jul. 14, 2014, which claims priority from European Patent Application No. 13177879.7, filed Jul. 24, 2013 incorporated herein by reference.

FIELD OF THE INVENTION

The present invention relates to a process for preparing a chlorine comprising catalyst. The catalyst is suitable for use in producing normally gaseous, normally liquid and optionally normally solid hydrocarbons from synthesis gas generally provided from a hydrocarbonaceous feed, for example a Fischer-Tropsch process. The invention further relates to the catalyst and the use thereof in Fischer-Tropsch processes.

BACKGROUND

The Fischer-Tropsch process can be used for the conversion of synthesis gas (from hydrocarbonaceous feed stocks) into liquid and/or solid hydrocarbons. Generally, the feed stock (e.g. natural gas, associated gas and/or coal-bed methane, heavy and/or residual oil fractions, coal, biomass) is converted in a first step into a mixture of hydrogen and carbon monoxide (this mixture is often referred to as synthesis gas or syngas). The synthesis gas is then fed into a reactor where it is converted in one or more steps over a suitable catalyst at elevated temperature and pressure into paraffinic compounds and water. The obtained paraffinic compounds range from methane to high molecular weight hydrocarbons. The obtained high molecular weight hydrocarbons can comprise up to 200 carbon atoms, or, under particular circumstances, even more carbon atoms.

Numerous types of reactor systems have been developed for carrying out the Fischer-Tropsch reaction. For example, Fischer-Tropsch reactor systems include fixed bed reactors, especially multi-tubular fixed bed reactors, fluidised bed reactors, such as entrained fluidised bed reactors and fixed fluidised bed reactors, and slurry bed reactors such as three-phase slurry bubble columns and ebulated bed reactors.

Catalysts used in the Fischer-Tropsch synthesis often comprise a carrier based support material and one or more metals from Group 8-10 of the Periodic Table, preferably from the cobalt or iron groups, optionally in combination with one or more metal oxides and/or metals as promoters selected from zirconium, titanium, chromium, vanadium and manganese, more preferably manganese and rhenium, most preferably manganese. Such catalysts are known in the art and have been described for example, in the specifications of WO 9700231A and U.S. Pat. No. 4,595,703.

One of the limitations of a Fischer-Tropsch process is that the activity of the catalyst will, due to a number of factors, decrease over time. There is a need for catalysts that are stable over a long period of time.

During a Fischer-Tropsch process paraffinic compounds ranging from methane to high molecular weight hydrocarbons are formed. There is a need for catalysts that have a high selectivity towards $C_5+$ hydrocarbons.

The formation of carbon dioxide during a Fischer-Tropsch process is preferably kept as low as possible. There is a need for catalysts that have a low selectivity towards $CO_2$.

The Fischer-Tropsch reaction is very exothermic and temperature sensitive. In consequence, careful temperature control is required to maintain optimum operation conditions and desired hydrocarbon product selectivity. The fact that the reaction is very exothermic also has the consequence that when temperature control is not adequate, the reactor temperature can increase very quickly, which carries the risk of a reactor runaway. A reactor runaway may result in highly increased temperatures at one or more locations in the reactor. A reactor runaway is a most undesirable phenomenon, as it may result in catalyst deactivation which necessitates untimely replacement of the catalyst, causing reactor downtime and additional catalyst cost.

A high-speed stop may, for example, be required when the temperature in the Fischer-Tropsch reactor increases to an unacceptable value either locally or over the entire reactor, when there is an interruption in the gas flow, or in the case of other unforeseen circumstances. When there is a threat of a runaway, it is often wise to stop the reaction as quick as possible. Several processes for carrying out a high-speed stop in a Fischer-Tropsch reactor have been developed.

When a high-speed stop is carried out in a fixed-bed reactor, a raise in temperature, culminating in a process-side temperature peak is often observed. If a process-side temperature peak is observed, it is usually observed at the upstream side of the catalyst bed. A process-side temperature peak is generally caused by a decrease in gas space velocity which leads to an increased conversion, accompanied by increased heat formation, and simultaneously to a decrease in heat removal capacity.

The peak temperature increase can be minimised by choosing the right method for the high-speed stop, but it will nevertheless have some influence on the catalyst. Therefore, there is need for a Fischer-Tropsch catalyst which is well able to withstand any kind of process for carrying out a high-speed stop in a Fischer-Tropsch process.

It is one object of the present invention to provide a process for preparing an improved cobalt comprising Fischer-Tropsch catalyst.

U.S. Pat. No. 3,842,121 discloses a catalyst capable of synthesizing various hydrocarbons from a mixture of hydrogen and carbon monoxide. With the catalyst a $C_2$ hydrocarbon, such as ethylene and ethane can be obtained in high conversion. In Example 4 of U.S. Pat. No. 3,842,121 a catalyst prepared from cobalt chloride, graphite and potassium mainly produces $C_2$ hydrocarbons and shows a higher selectivity towards $C_2$ hydrocarbons as compared to a catalyst prepared from graphite and potassium.

M. P. Rosynek et al. in Applied Catalysis, 73 (1991) 97-112 tested silica-supported cobalt catalysts that were prepared using cobalt nitrate, cobalt chloride, or cobalt acetate. They report that there appeared to be no direct relationship between catalytic activity and the ease or extent of metal reduction. When directly reduced for 16 hours at 400° C., and not calcined at a higher temperature before reduction, catalysts prepared with cobalt chloride showed a very low initial activity in the Fischer-Tropsch reaction. The initial activity was much lower than the initial activity of catalysts prepared with cobalt nitrate or cobalt acetate, and may be due to residual surface chloride. After calcination for 16 hours at 500° C. and reduction for 16 hours at 400° C. catalysts prepared with cobalt chloride showed a slightly lower selectivity as compared to catalysts prepared with cobalt nitrate or cobalt acetate.

J. W. Bae et al. in Journal of Molecular Catalysis A: Chemical 311 (2009) 7-16 discuss a preparation method for cobalt comprising catalysts. The support of the catalysts is aluminum phosphate ($AlPO_4$). The cobalt was applied by means of impregnation using cobalt nitrate, cobalt acetate or cobalt chloride. The residue of chlorine of 3.8 wt % on the catalysts prepared using cobalt chloride was not removed efficiently even after calcination for 5 hours at 500° C. After activation at for 12 hours at 400° C. with a hydrogen comprising gas the catalysts prepared using cobalt chloride showed higher methane and $C_2$-$C_4$ selectivities, and lower $C_5$-$C_7$ and $C_8$+ selectivities, as compared to the catalysts prepared using cobalt nitrate or cobalt acetate.

US2010/0048742A1 relates to cobalt comprising Fischer-Tropsch catalysts. The support consists of aluminum and lithium. In case a precipitated alumina is used to prepare the catalyst, US2010/0048742A1 teaches to wash the alumina to remove contaminants such as chlorine. Additionally, the lithium oxide containing support may be washed to remove chlorine, prior to combining the support with cobalt compounds. US2010/0048742A1 teaches that chlorine contaminants may reduce the Fischer-Tropsch catalyst activity and/or selectivity towards $C_5$+ hydrocarbons.

WO2008071640A2 describes a method of preparing a Fischer-Tropsch catalyst. In step (a) a promoter is contacted with a carrier material, step (b) is a drying step, and in step (c) cobalt is added. The promoter preferably is manganese. In one embodiment a minor amount of cobalt is already added in step (a) of the process of WO2008071640A2, followed by adding a further amount of cobalt in step (c) of the process. When manganese and cobalt are added in step (a), the weight of the cobalt atoms preferably is less than 10 wt % calculated on the total weight of cobalt and manganese atoms that is contacted with the carrier material in step (a). The major amount of cobalt is always applied in step (c) of the process of WO2008071640A2. A long list of possible cobalt sources is indicated for step (c).

WO8601500A1 discloses a method in which cobalt is impregnated on a carbon support, for example using cobalt nitrate. A small amount of chlorine is applied using a non-metallic chlorine compound, for example ammonium chloride. WO8601500A1 explains that the disclosed method is particularly useful when applied to catalysts comprising cobalt or iron on a support whereby the support is a carbon having a BET surface area of at least 100 m2/g, a ratio of BET to basal plane surface area not greater than 4:1, and a ratio of basal plane surface area to edge surface area of at least 10:1. WO8601500A1 teaches against the use of a metallic chlorine compound on a carbon support.

According to one aspect of the present invention, there is provided a process for preparing a chlorine comprising catalyst, comprising the following steps:
(a) providing a Fischer-Tropsch catalyst comprising:
   titania
   at least 5 weight percent cobalt, preferably in the range of between 5 to 35 weight percent cobalt, more preferably in the range of between 10 to 35 weight percent cobalt, even more preferably in the range of between 15 to 30 weight percent cobalt, still more preferably in the range of between 15 to 25 weight percent cobalt, calculated on the total weight of the catalyst
   in the range of between to 0.1 to 15 weight percent promoter, preferably in the range of between 0.5 to 5 weight percent promoter calculated on the total weight of the catalyst, whereby the promoter preferably comprises manganese, rhenium, Group 8-10 noble metals, or mixtures thereof, more preferably manganese or rhenium, most preferably manganese;
(b) impregnating the catalyst with one or more solutions comprising chloride ions until the catalyst comprises 0.13-10 weight percent of the element chlorine, calculated on the total weight of the catalyst;
(c) heating the impregnated catalyst at a temperature in the range of 100 to 500° C., preferably 100 to 400° C., more preferably 100 to 350° C., for at least 5 minutes up to 2 days, preferably for at least 15 minutes up to 1 day, more preferably for at least 15 minutes up to 5 hours.

Preferably the catalyst is impregnated in step (b) impregnated in step (b) until the catalyst comprises 0.13-6, preferably 0.15-6, more preferably 0.15-3, even more preferably 0.15-2.5, still more preferably 0.15-2 weight percent of the element chlorine, calculated on the total weight of the catalyst.

A chlorine comprising catalyst prepared according to the present invention preferably comprises 0.13-3, more preferably 0.15-3, even more preferably 0.15-2, still more preferably 0.15-1, still more preferably 0.15-1, most preferably 0.15-0.7 weight percent of the element chlorine, calculated on the total weight of the catalyst.

A chlorine comprising catalyst prepared according to the present invention preferably comprises 0.2-1, more preferably 0.2-0.7 weight percent of the element chlorine, calculated on the total weight of the catalyst.

During a method according to the present invention chlorine may or may not be removed from the catalyst during step (c), depending on the amount of chlorine applied in step (b) and the heating temperature and duration of step (c). In a preferred embodiment the desired amount of chlorine is applied in step (b) and the heating temperature in step (c) is 100 to 350° C., and the catalyst is heated for at least 15 minutes up to 1 day, preferably for at least 15 minutes up to 5 hours.

The amount of the element chlorine on the obtained catalyst can be regulated by choosing the amount of chlorine applied in step (b) within the ranges provided in this document for step (b), and by choosing the temperature and duration of the heating of step (c) within the ranges provided in this document for step (c). This is simple for a person skilled in the art. Additionally, the examples below illustrate how this may be performed.

The process of the present invention preferably is a process wherein the temperature and duration of the heating of step (c) are sufficient to effect the preparation of a catalyst comprising 0.13-3, more preferably 0.15-3, even more preferably 0.15-2, still more preferably 0.15-1, most preferably 0.2-1 weight percent of the element chlorine, calculated on the total weight of the catalyst.

The process of the present invention more preferably is a process wherein the amount of chlorine applied in step (b) and the temperature and duration of the heating of step (c) are sufficient to effect the preparation of a catalyst comprising 0.13-3, more preferably 0.15-3, even more preferably 0.15-2, still more preferably 0.15-1, most preferably 0.2-1 weight percent of the element chlorine, calculated on the total weight of the catalyst.

The invention further relates to a catalyst that is prepared according to the method of the present invention, said catalyst comprising 0.13-3, more preferably 0.15-3, even more preferably 0.15-2, still more preferably 0.15-1, most preferably 0.2-1 weight percent of the element chlorine, calculated on the total weight of the catalyst. The invention further relates to the use of such a catalyst in a Fischer-Tropsch process.

It was found that catalysts can be prepared that are stable over a long period of time. Another advantage is that catalysts can be prepared showing an increased selectivity towards $C_5+$ hydrocarbons as compared to similar catalysts that have been prepared without chlorine. A further advantage is that catalysts can be prepared showing a decreased selectivity towards carbon dioxide as compared to similar catalysts that have been prepared without chlorine. Additionally, catalysts can be prepared that are well able to withstand a high-speed stop in a Fischer-Tropsch process.

The Fischer-Tropsch catalyst comprising cobalt and titania which is provided in step (a), and which is impregnated with a solution comprising chloride ions in step (b) of the process of the present invention, preferably is a calcined catalyst. More preferably the cobalt and titania comprising calcined catalyst provided in step (a) has been calcined at a temperature between 350 and 700° C., more preferably between 450 and 700° C., even more preferably between 500 and 650° C., for at least 1 minute up to 2 days, preferably for at least 15 minutes up to 1 day.

The Fischer-Tropsch catalyst comprising cobalt and titania which is provided in step (a) preferably comprises cobalt oxide ($Co_3O_4$). Such a catalyst particle can normally be obtained by treating a cobalt and titania comprising particle with an oxygen-containing gas at a temperature between 20 and 600° C., preferably between 100 and 450° C., more preferably between 200 and 450° C., for about 12 hours. The oxygen containing gas may, for example, be pure oxygen, oxygen enriched air (preferably containing 25 to 70 volume % oxygen), air (containing about 21 volume % oxygen), or air diluted with inert e.g. with nitrogen. Preferably the oxygen containing gas is air.

In one embodiment, the Fischer-Tropsch catalyst comprising cobalt and titania which is provided in step (a) additionally comprises manganese, preferably manganese oxide ($MnO_2$). In one embodiment, the Fischer-Tropsch catalyst comprising cobalt and titania which is provided in step (a) comprises the spinel $(Co,Mn)_3O_4$. The catalyst may comprise cobalt oxide ($Co_3O_4$), manganese oxide ($MnO_2$) and the spinel $(Co,Mn)_3O_4$.

A solution comprising chloride ions which is impregnated in step (b) preferably is a solution comprising one or more metal salts of chloride, hydrochloric acid (HCl), one or more organic chloride compounds, or a combination thereof.

Suitable organic chloride compounds that may be impregnated in step (b) of the process have the potential to release a chloride ion when in solution.

The organic chloride compounds that may be impregnated in step (b) of the process preferably is/are acyl chlorides, such as propionic acid chloride; alkyl ammonium chlorides, such as tetra butyl ammonium chloride; or mixtures thereof.

The metal salt(s) of chloride that may be impregnated in step (b) of the process preferably is/are a chloride of manganese, cobalt, vanadium, titanium, silver, gold, zinc, platinum, palladium, zirconium, ruthenium, rhenium, rhodium, chromium, nickel, iron, osmium, or iridium or mixtures thereof. More preferably the metal salt(s) of chloride is/are a chloride of manganese, cobalt, silver, gold or zinc or mixtures thereof. Even more preferably the metal salt(s) of chloride is/are a chloride of manganese or cobalt, or mixtures thereof.

The metal salt(s) of chloride that may be impregnated in step (b) of the process more preferably is/are a chloride of manganese such as manganese chloride ($MnCl_2$) and manganese chloride tetrahydrate ($Mn(H_2O)_4Cl_2$); a chloride of cobalt such as cobalt chloride ($CoCl_2$), hydrated cobalt chloride ($Co(H_2O)_6Cl_2$) and hexamminecobalt chloride ($[Co(NH_3)_6]Cl_3$); a chloride of silver such as silver chloride (AgCl); or a chloride of gold such as auric chloride ($AuCl_3$), gold chloride (AuCl) and chloroauric acid ($HAuCl_4$); zinc chloride (ZnCl) or mixtures thereof, more preferably manganese chloride ($MnCl_2$) and/or cobalt chloride ($CoCl_2$).

The solutions used for impregnating metal salt(s) of chloride or organic chloride compound(s) in step (b) may comprise any solvent. The solvent may be any of suitable liquids known in the art, for example: water; ammonia, alcohols, such as ethanol; ketones, such as acetone; ethers, such as diethylether, and mixtures of the aforesaid liquids. A most convenient and preferred liquid is water.

When a solution comprising one or more metal salts of chloride and/or one or more organic chloride compounds is used in step (b), the concentration of the salt(s) of chloride in the solution may be chosen as desired. A preferred solution has a concentration of chlorine atoms in the range of between 0.5 to 25 gram per liter, but lower and higher concentrations are also suitable.

In step (b) the catalyst is impregnated with a solution comprising chloride ions, until the catalyst comprises 0.13-10 weight percent of the element chlorine, calculated on the total weight of the catalyst. Preferably the catalyst is impregnated until the catalyst comprises 0.13-6, preferably 0.15-6, more preferably 0.15-3 weight percent of the element chlorine, calculated on the total weight of the catalyst.

If desired, the impregnation step (b) may be performed by impregnating the catalyst one or more times. When the impregnation step (b) is performed by impregnating the catalyst more than once, the catalyst may, if desired, be dried and/or heated between such impregnations.

The catalyst may be impregnated with one or more metal salts of chloride in step (b). This impregnation may be performed using one or more solutions prepared from a non-metallic salt of chloride and/or a chloride acid and/or a metal salt, which may be a metal salt of chloride, and/or a metal hydroxide.

A non-metallic salt of chloride may be an inorganic salt of chloride, for example ammonium chloride, or an organic salt of chloride. An example of a chloride acid is hydrogen chloride (HCl). A metal salt may be a metal chloride, for example cobalt chloride, or a metal salt not comprising chlorine, for example cobalt nitrate or manganese nitrate. Examples of a metal hydroxide are cobalt hydroxide and manganese hydroxide.

For example, the impregnation may be performed using a solution comprising cobalt chloride, followed by using a solution comprising manganese chloride. Or, the impregnation may be performed using a solution prepared from two different metal salts of chloride, for example cobalt chloride and manganese chloride. Additionally or alternatively the impregnation may, for example, be performed using a solution prepared by mixing a salt, for example NaCl, with a metal hydroxide, for example Co(OH)2.

In step (b) preferably a metal salt of chloride or an inorganic salt of chloride is used. Most preferably a metal salt of chloride is used. Preferably one type of solution comprising one or more metal salts of chloride is used in the impregnation step (b). For example, the solution used in step (b) may be cobalt chloride and/or manganese chloride. If desired, different types of solutions comprising one or more metal salts of chloride may be used. For example, during the impregnation step (b) the catalyst may first be impregnated with a solution comprising manganese chloride ($MnCl_2$) and then with a solution comprising cobalt chloride ($CoCl_2$).

In one embodiment a solution comprising a non-metallic salt of chloride and a solution comprising a metal salt are impregnated. When both have been impregnated the catalyst will contain metal ions and chloride ions, and will thus have been impregnated with a metal salt of chloride. For example: if the catalyst is first impregnated with ammonium chloride and then with cobalt nitrate, or vice versa, the catalyst is impregnated with cobalt chloride.

In another embodiment a solution comprising an acid of chloride and a solution comprising a metal salt are impregnated. When both have been impregnated the catalyst will contain metal ions and chloride ions, and will thus have been impregnated with a metal salt of chloride. For example: if the catalyst is first impregnated with hydrogen chloride, or with hydrochloric acid, and then with cobalt nitrate, or vice versa, the catalyst is impregnated with cobalt chloride.

After impregnating in step (b) until the catalyst comprises 0.13-10 weight percent of the element chlorine, the impregnated catalyst is heated in step (c) at a temperature in the range of 100 to 500° C., preferably 100 to 400° C., more preferably 100 to 350° C., for at least 5 minutes up to 2 days, preferably for at least 15 minutes up to 1 day, more preferably for at least 15 minutes up to 5 hours.

During the heating (c) step a part of the metal salt(s) of chloride impregnated on the catalyst may be removed.

After the heating step (c) the catalyst preferably comprises 0.13-3, more preferably 0.15-3, even more preferably 0.15-2, still more preferably 0.15-1 weight percent of the element chlorine, calculated on the total weight of the catalyst.

The process of the current invention is suitable for fixed bed catalysts, slurry catalysts, i.e. powder like catalysts, and immobilized slurry catalyst, for example wire structures coated with catalyst material. The catalyst provided in step (a) of the process of the invention preferably comprises catalyst particles which are fixed bed particle(s) larger than 1 mm, or immobilised slurry particles larger than 1 mm.

Examples of suitable immobilized slurry catalysts to which the process of the present invention can be applied are catalysts with a size larger than 1 mm which catalysts comprise a substrate, for example a metal substrate such as a stainless steel wire substrate, and catalyst material comprising titania and cobalt.

The immobilized slurry catalyst may, for example, be in the form of a fixed structure (or arranged packing) such as gauze, corrugated sheet material that may or may not be perforated with holes, woven or non-woven structure, honeycomb, foam, sponge, mesh, webbing, foil construct, woven mat form, wire, ball, cylinder, cube, sphere, ovoid, monolith, or any combination of these.

The present invention especially relates to a process that can be used to prepare fixed bed catalysts, such as pellets and extrudates larger than 1 mm Particles having a particle size of at least 1 mm are defined as particles having a longest internal straight length of at least 1 mm.

The heating step (c) may, for example, be performed in air, under hydrogen or a hydrogen comprising gas, or under an inert gas, preferably in air.

In one embodiment of the process according to the invention, the catalyst may be reduced with hydrogen or a hydrogen comprising gas after the impregnation step. The catalyst may be reduced with hydrogen or a hydrogen comprising gas during and/or after the heating step. Reduction may be formed, for example, at a temperature in the range of between 200 and 350° C. for 5 minutes up to several days.

The catalyst preferably is reduced with hydrogen or a hydrogen comprising gas after the heating step. In an even more preferred embodiment, heating step (c) is performed in air and in a later step the catalyst is reduced with hydrogen or a hydrogen comprising gas.

Hence, in a process according to the present invention, the catalyst may be reduced with hydrogen or a hydrogen comprising gas after the impregnation step (b), which may preferably be performed during and/or after the heating step (c), more preferably after the heating step (c).

The present invention also provides a catalyst that can be obtained by the processes of the current invention.

The Fischer-Tropsch catalyst provided in step (a) of the present invention comprises the refractory oxide titania, preferably porous titania, as carrier material. The carrier may comprise up to 10 weight percent of another refractory oxide, calculated on the total weight of carrier material. The carrier of the catalyst may, for example, comprise silica, alumina, zirconia, ceria, gallia and mixtures thereof, especially silica and/or alumina, in addition to the titania. Preferably more than 90 weight percent of the carrier material consists of titania, more preferably more than 95 weight percent, calculated on the total weight of the carrier material. As an example of a suitable titania can be mentioned the commercially available Titanium Dioxide P25 ex Evonik Industries.

The catalytically active metal in the catalyst is cobalt. Cobalt may be added to the carrier in the form of, for example, cobalt hydroxide, CoOOH, cobalt oxide, a co-precipitate of cobalt and manganese hydroxide, a cobalt nitrite, or a cobalt ammonium complex, for example cobalt ammonium carbonate. The catalyst may also include one or more further components, such as promoters and/or co-catalysts.

Suitable co-catalysts include one or more metals such as iron, nickel, or one or more noble metals from Group 8-10 of the Periodic Table of Elements. Preferred noble metals are platinum, palladium, rhodium, ruthenium, iridium and osmium. Such co-catalysts are usually present in small amounts.

References to "Groups" and the Periodic Table as used herein relate to the new IUPAC version of the Periodic Table of Elements such as that described in the 87th Edition of the Handbook of Chemistry and Physics (CRC Press).

Typically, the amount of catalytically active metal present in the catalyst may range from 1 to 100 parts by weight per 100 parts by weight of carrier material, preferably from 3 to 50 parts by weight per 100 parts by weight of carrier material.

The catalyst that is provided in step (a) of the present invention preferably comprises titania and in the range of between 3 to 40 weight percent cobalt, preferably in the range of between 5 to 30 weight percent cobalt, more preferably in the range of between 15 to 25 weight percent cobalt calculated on the total weight of the catalyst.

The catalyst may further comprise one or more promoters. One or more metals or metal oxides may be present as promoters, more particularly one or more d-metals or d-metal oxides. Suitable metal oxide promoters may be selected from Groups 2-7 of the Periodic Table of Elements, or the actinides and lanthanides. In particular, oxides of magnesium, calcium, strontium, barium, scandium, yttrium, lanthanum, cerium, titanium, zirconium, hafnium, thorium, uranium, vanadium, chromium and manganese are most suitable promoters. Suitable metal promoters may be selected from Groups 7-10 of the Periodic Table of Elements.

Manganese, rhenium and Group 8-10 noble metals are particularly suitable as promoters, and are preferably provided in the form of a salt or hydroxide.

The promoter, if present in the catalyst, is typically present in an amount of from 0.001 to 100 parts by weight per 100 parts by weight of carrier material, preferably 0.05 to 20, more preferably 0.1 to 15. It will however be appreciated that the optimum amount of promoter may vary for the respective elements which act as promoter.

One particularly preferred Fischer-Tropsch catalyst comprises a manganese or vanadium promoter.

The catalyst that is provided in step (a) of the present invention preferably comprises:
titania
at least 5 weight percent cobalt, calculated on the total weight of the catalyst
in the range of between to 0.1 to 15 weight percent promoter, preferably in the range of between 0.5 to 5 weight percent promoter calculated on the total weight of the catalyst,
whereby the promoter preferably comprises manganese, rhenium, Group 8-10 noble metals, or mixtures thereof, more preferably manganese.

The catalyst that is provided in step (a) of the present invention more preferably comprises:
titania,
in the range of between 5 to 40 weight percent cobalt, preferably in the range of between 5 to 30 weight percent cobalt, more preferably in the range of between 15 to 25 weight percent cobalt calculated on the total weight of the catalyst
in the range of between to 0.1 to 15 weight percent promoter, preferably in the range of between 0.5 to 5 weight percent promoter calculated on the total weight of the catalyst,
whereby the promoter preferably comprises manganese, rhenium, Group 8-10 noble metals, or mixtures thereof, more preferably manganese.

The catalyst that is provided in step (a) of the present invention preferably comprises in the range of between to 0.1 to 15 weight percent manganese, rhenium, Group 8-10 noble metals, or mixtures thereof, more preferably in the range of between 0.5 to 5 weight percent manganese, rhenium, Group 8-10 noble metals, or mixtures thereof, even more preferably 0.5 to 5 weight percent manganese calculated on the total weight of the catalyst.

When fresh prepared, the catalyst may have been shaped or formed by means of spray drying, pelletizing, (wheel) pressing, extrusion, or application on a metal support (like a metal wire or a metal flake).

The catalytically active metal and/or any promoter may have been added to the carrier material before or after shaping.

For example, in case of fixed bed particles, a cobalt compound, preferably cobalt hydroxide, CoOOH, cobalt oxide, or a co-precipitate of cobalt and manganese hydroxide, may be mixed with a refractory metal oxide, followed by extrusion. Or, a refractory metal oxide may be extruded, and in a later step the extrudates may be impregnated with a cobalt compound, preferably with a cobalt salt that is soluble in water and/or ethanol.

When a carrier material is shaped, it may be advantageous to add a binder material, for example to increase the mechanical strength of the catalyst. Additionally or alternatively, a liquid may be added to the carrier material before or during its shaping. The liquid may be any of suitable liquids known in the art, for example: water; ammonia, alcohols, such as methanol, ethanol and propanol; ketones, such as acetone; aldehydes, such as propanol and aromatic solvents, such as toluene, and mixtures of the aforesaid liquids. A most convenient and preferred liquid is water. The liquid may include viscosity improvers such as a polyvinyl-alcohol.

In case of extrusion, one may want to improve the flow properties of the carrier material. In that case it is preferred to include one or more flow improving agents and/or extrusion aids prior to extrusion. Suitable additives include fatty amines, quaternary ammonium compounds, polyvinyl pyridine, sulphoxonium, sulphonium, phosphonium and iodonium compounds, alkylated aromatic compounds, acyclic mono-carboxylic acids, fatty acids, sulphonated aromatic compounds, alcohol sulphates, ether alcohol sulphates, sulphated fats and oils, phosphonic acid salts, polyoxyethylene alkylphenols, polyoxyethylene alcohols, polyoxyethylene alkylamines, polyoxyethylene alkylamides, polyacrylamides, polyols and acetylenic glycols. Preferred additives are sold under the trademarks Nalco and Superfloc.

To obtain strong extrudates, it is preferred to include, prior to extrusion, at least one compound which acts as a peptising agent for the refractory metal oxide. For example, a peptising agent for titania may be included prior to extrusion. Suitable peptising agents are well known in the art and include basic and acidic compounds. Examples of basic compounds are ammonia, ammonia-releasing compounds, ammonium compounds or organic amines In case of a calcination step after shaping, such basic compounds are removed upon calcination and are not retained in the extrudates. This is advisable as such basic compounds may impair the catalytic performance of the final product. Preferred basic compounds are organic amines or ammonium compounds. A most suitable organic amine is ethanol amine. Suitable acidic peptising agents include weak acids, for example formic acid, acetic acid, citric acid, oxalic acid, and propionic acid.

Optionally, burn-out materials may be included prior to extrusion, in order to create macropores in the resulting extrudates. Suitable burn-out materials are commonly known in the art.

The total amount of flow-improving agents/extrusion aids, peptising agents, and burn-out materials in the carrier material to be extruded preferably is in the range of from 0.1 to 20% by weight, more preferably from 0.5 to 10% by weight, on the basis of the total weight of the mixture.

After shaping, the carrier material, optionally including further components, may be strengthened by calcination thereof in a manner known in the art. The calcination temperature depends on the carrier material used. Titania is preferably calcined at a temperature between 350 and 700° C., more preferably between 450 and 700° C., more preferably between 500 and 650° C. A calcination step is nevertheless optional.

A fresh prepared catalyst may be activated. Activation may be performed by reducing the catalytically active metal of the catalyst. Activation of a fresh prepared catalyst, whether it is a powder like slurry catalyst, fixed bed catalyst, or immobilised slurry catalyst, can be carried out in any known manner and under conventional conditions. For example, the catalyst may be activated by contacting it with hydrogen or a hydrogen-containing gas, typically at temperatures of about 200° to 350° C.

The catalyst that is provided in step (a) may be a deactivated catalyst, i.e. it may be a catalyst that has been used in a Fischer-Tropsch reaction and that lost a part or all of its activity. The catalyst that is provided in step (a) may be a deactivated catalyst that has been subjected to a regeneration method. The catalyst that is provided in step (a) may be a recycled catalyst.

The present invention also provides a process comprising the use of a catalyst according to the invention in a Fischer-Tropsch synthesis process. The invention relates to a process for performing a Fischer-Tropsch reaction comprising the following steps:
  providing syngas to a reactor, said reactor comprising catalyst particles that have been prepared using a process according to the present invention;
  providing the following process conditions in the reactor: a temperature in the range from 125 to 350° C., a pressure in the range from 5 to 150 bar absolute, and a gaseous hourly space velocity in the range from 500 to 10000 Nl/l/h;
  removing Fischer-Tropsch product from the reactor.

The Fischer-Tropsch process is well known to those skilled in the art and involves synthesis of hydrocarbons from syngas, by contacting the syngas at reaction conditions with the Fischer-Tropsch catalyst.

The synthesis gas can be provided by any suitable means, process or arrangement. This includes partial oxidation and/or reforming of a hydrocarbonaceous feedstock as is known in the art. To adjust the $H_2/CO$ ratio in the syngas, carbon dioxide and/or steam may be introduced into the partial oxidation process. The $H_2/CO$ ratio of the syngas is suitably between 1.5 and 2.3, preferably between 1.6 and 2.0.

The syngas comprising predominantly hydrogen, carbon monoxide and optionally nitrogen, carbon dioxide and/or steam is contacted with a suitable catalyst in the catalytic conversion stage, in which the hydrocarbons are formed. Suitably at least 70 v/v % of the syngas is contacted with the catalyst, preferably at least 80%, more preferably at least 90%, still more preferably all the syngas.

A steady state catalytic hydrocarbon synthesis process may be performed under conventional synthesis conditions known in the art. Typically, the catalytic conversion may be effected at a temperature in the range of from 100 to 600° C., preferably from 150 to 350° C., more preferably from 175 to 275° C., most preferably 200 to 260° C. Typical total pressures for the catalytic conversion process are in the range of from 5 to 150 bar absolute, more preferably from 5 to 80 bar absolute. In the catalytic conversion process mainly $C_5+$ hydrocarbons are formed.

A suitable regime for carrying out the Fischer-Tropsch process with a catalyst comprising particles with a size of least 1 mm is a fixed bed regime, especially a trickle flow regime. A very suitable reactor is a multi-tubular fixed bed reactor.

Experimental
Measurement Method; Activity

Catalytic activities can be measured, for example, in a model Fischer-Tropsch reactor. The catalytic activities measured may be expressed as space time yield (STY) or as an activity factor, whereby an activity factor of 1 corresponds to a space time yield (STY) of 100 g/l.hr at 200° C.

Part I; Titania/Manganese/Cobalt—Metal Salts of Cl
Sample Preparation

Fixed bed particles were prepared as follows. Mixtures were prepared containing titania powder, cobalt hydroxide, manganese hydroxide, water and several extrusion aids. The mixtures were kneaded. The mixtures were shaped using extrusion. The extrudates were dried and calcined. The obtained catalysts contained about 20 wt % cobalt and about 1 wt % of manganese.

A part of the catalyst particles was used as reference (Comparative Examples). As one or more of the ingredients used comprised chlorine or chlorine components, the Comparative Examples comprised a very small amount of chlorine. Several batches were prepared, with slightly different properties.

The comparative examples and the examples according to the invention were tested under different conditions. The experimental data can be compared per measurement set as presented below.

Examples 1-4

Catalyst particles which were prepared as described above were impregnated with different amounts of an aqueous solution of cobalt chloride ($CoCl_2$), and then heated to 300° C. for about 2 hours. The prepared catalysts comprised 0.2 to 0.7 weight percent of the element chlorine, calculated on the total weight of the catalyst. These catalysts are further referred to as Examples 1 to 4.

TABLE 1

| | Chlorine content |
|---|---|
| Comparative Example | 0.1 wt % |
| Example 1 | 0.2 wt % |
| Example 2 | 0.3 wt % |
| Example 3 | 0.4 wt % |
| Example 4 | 0.7 wt % |

A combination of XPS and Coulometry measurements showed that the chlorine was highly dispersed in the catalysts. This was the case for the Comparative Example as well as for Examples 1 to 4.

Activity Measurements

Samples from the comparative example and samples prepared according to the invention were reduced with a hydrogen comprising gas, and then the activity, selectivity and stability of the samples were determined during a Fischer-Tropsch reaction.

The activity of Examples 1 to 4 was determined against the Comparative Example in several tests. Table 2 shows the activity factor (AF) at the start of the Fischer-Tropsch reaction run (Sor), at the middle of the run (MoR), and at the end of the run (EoR). Additionally, Table 2 shows the total deactivation of the samples over the total duration of the run.

TABLE 2

| | Chlorine content | AF SoR | AF MoR | AF EoR | Deactivation |
|---|---|---|---|---|---|
| | | 0 h | 192 h | 407 h | |
| Comp. Ex. | 0.1 wt % | 1.59 | 1.40 | 1.10 | 31% |
| Example 1 | 0.2 wt % | 1.80 | 1.68 | 1.43 | 21% |
| Example 2 | 0.3 wt % | 1.83 | 1.69 | 1.50 | 18% |
| | | 0 h | 428 h | 884 h | |
| Comp. Ex. | 0.1 wt % | 1.75 | 1.43 | 1.29 | 27% |
| Example 3 | 0.4 wt % | 1.80 | 1.60 | 1.56 | 13% |
| | | 0 h | 653 h | 1113 h | |
| Comp. Ex | 0.1 wt % | 1.80 | 1.41 | 1.37 | 24% |
| Example 4 | 0.7 wt % | 1.44 | 1.26 | 1.19 | 18% |

From the activity data in Table 2 is clear that catalysts comprising 0.2, 0.3 or 0.4 wt % chlorine have a higher activity as compared to catalysts comprising 0.1 wt % chlorine. Additionally, these data show that catalysts comprising 0.2, 0.3, 0.4 or 0.7 wt % chlorine have a higher stability, i.e. show less deactivation over time, as compared to catalysts comprising 0.1 wt % chlorine.

Figure 1:
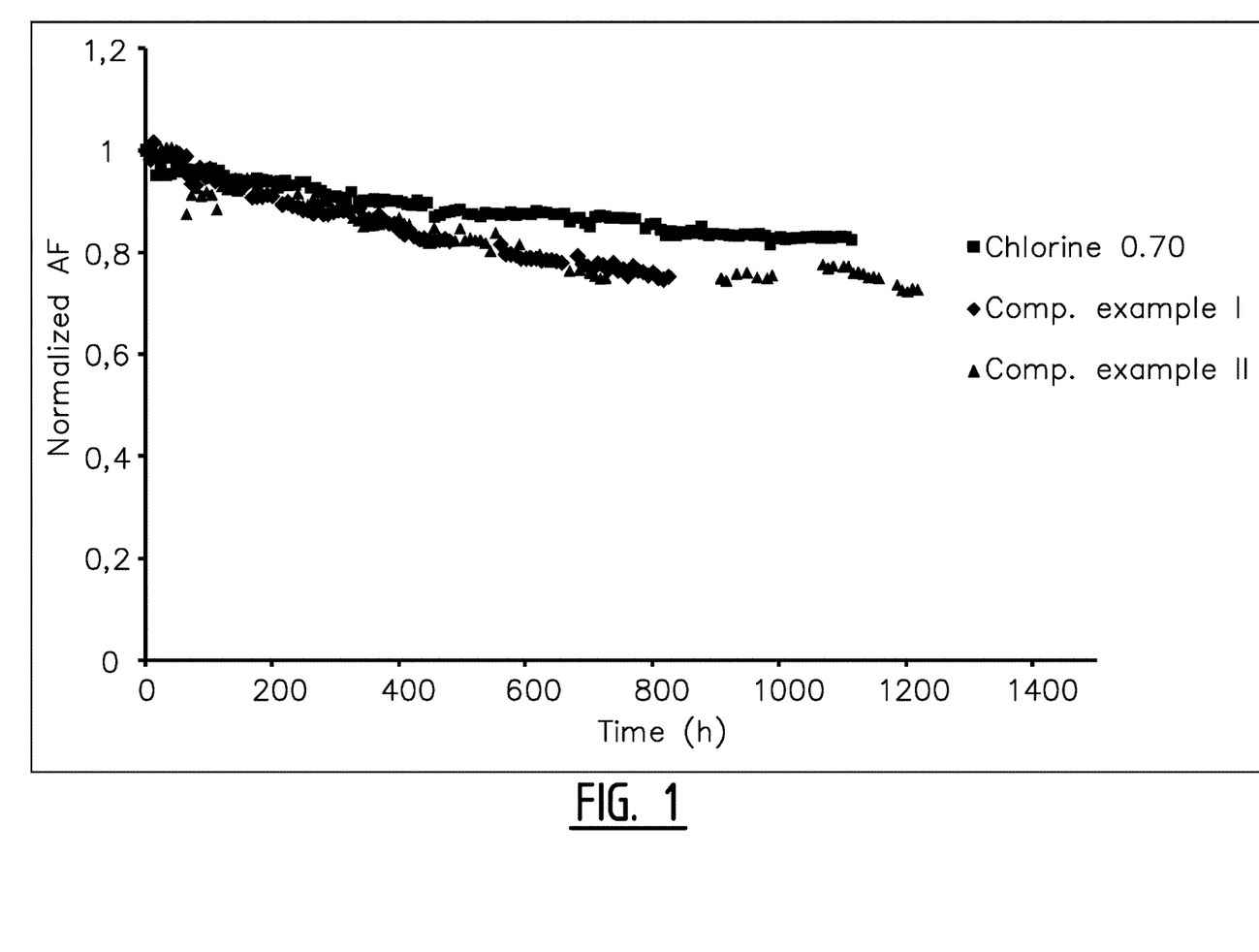
FIG. 1 is a graph of the activity factor plotted against time.
Figure 2:
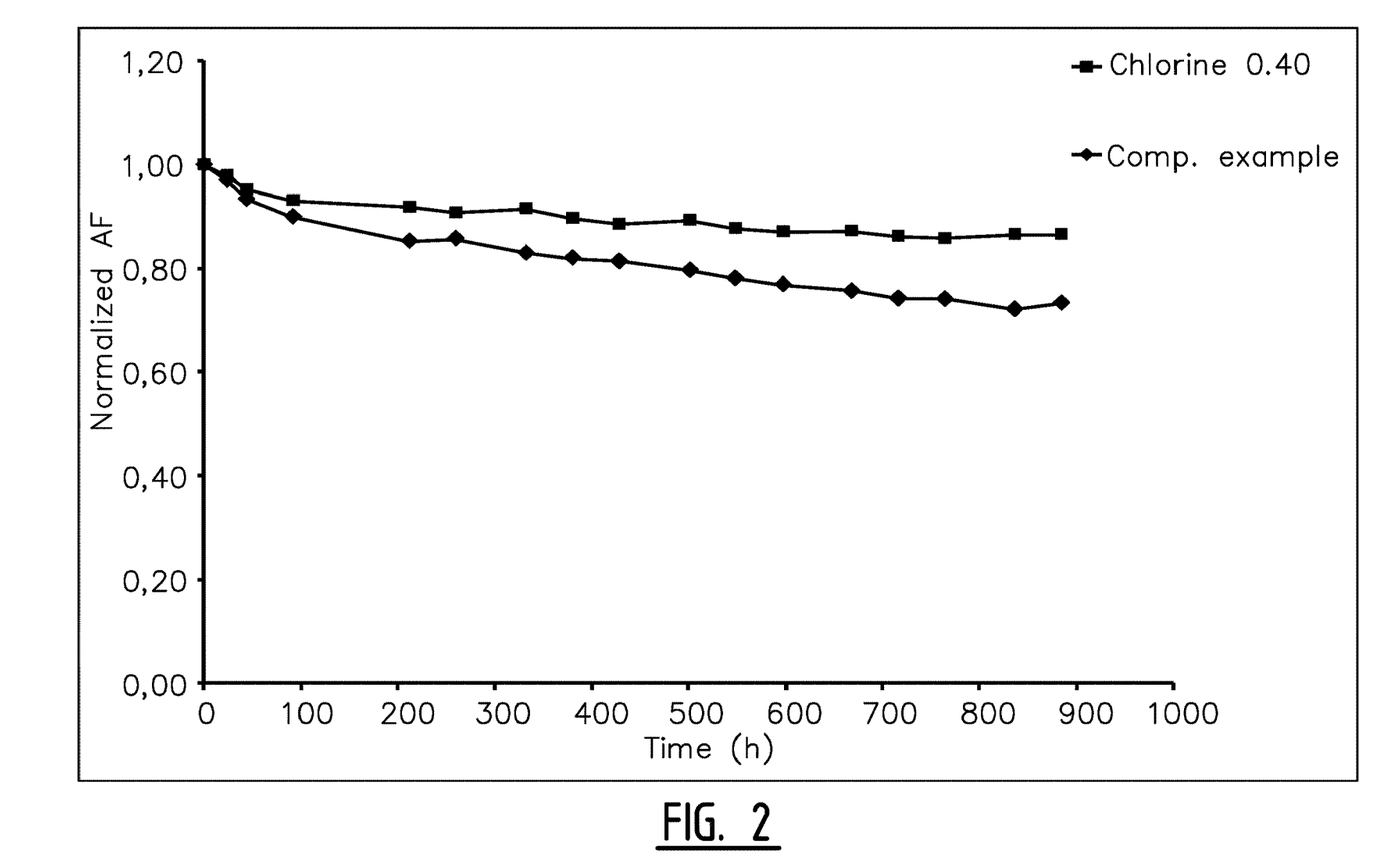
FIG. 2 is a graph of the activity factor plotted against time.
Figure 5:
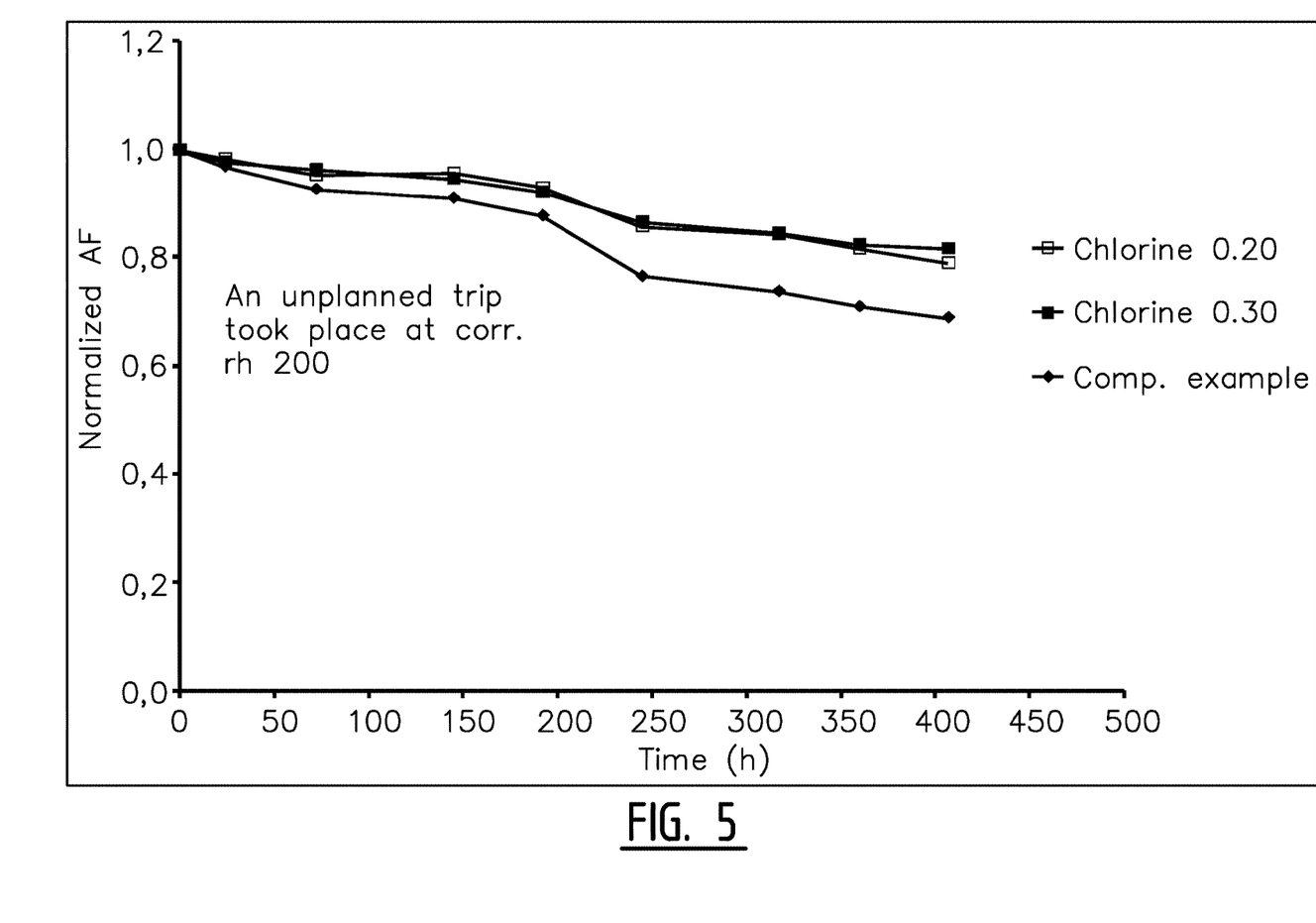
FIG. 5 is a graph of the activity factor plotted against time.

The activity and the stability of Examples 1 to 4 determined against the Comparative Example in several further tests. FIGS. 1 and 2 show that the catalysts comprising 0.7 and 0.4 wt % chlorine have a higher activity and a higher stability as compared to catalysts comprising 0.1 wt % chlorine. FIG. 5 shows that the catalysts comprising 0.2 and 0.3 wt % chlorine have a higher activity and a higher stability as compared to catalysts comprising 0.1 wt % chlorine.

Figure 3:
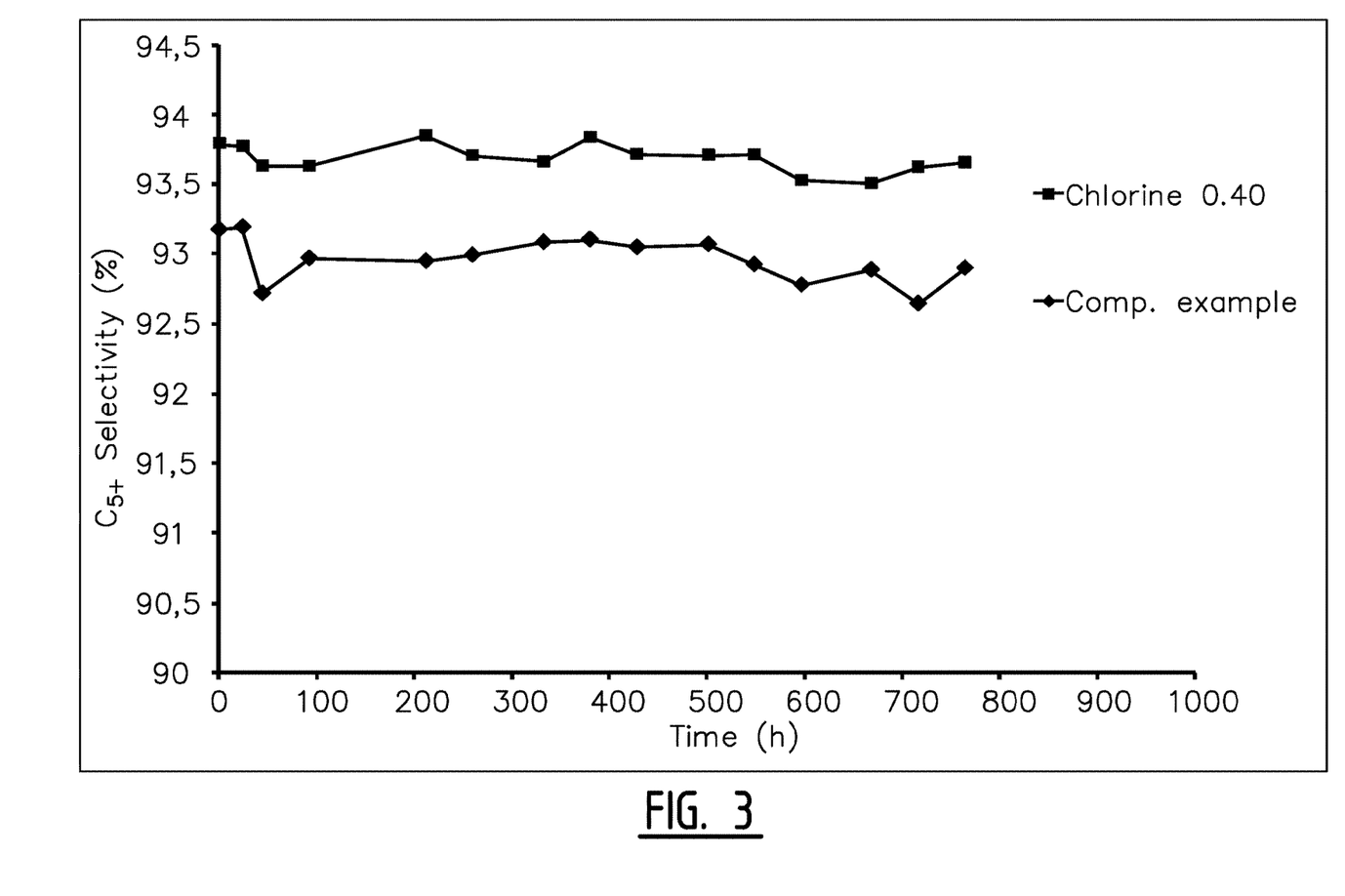
FIG. 3 is a graph of the C5+ selectivity factor against time.
Figure 4:
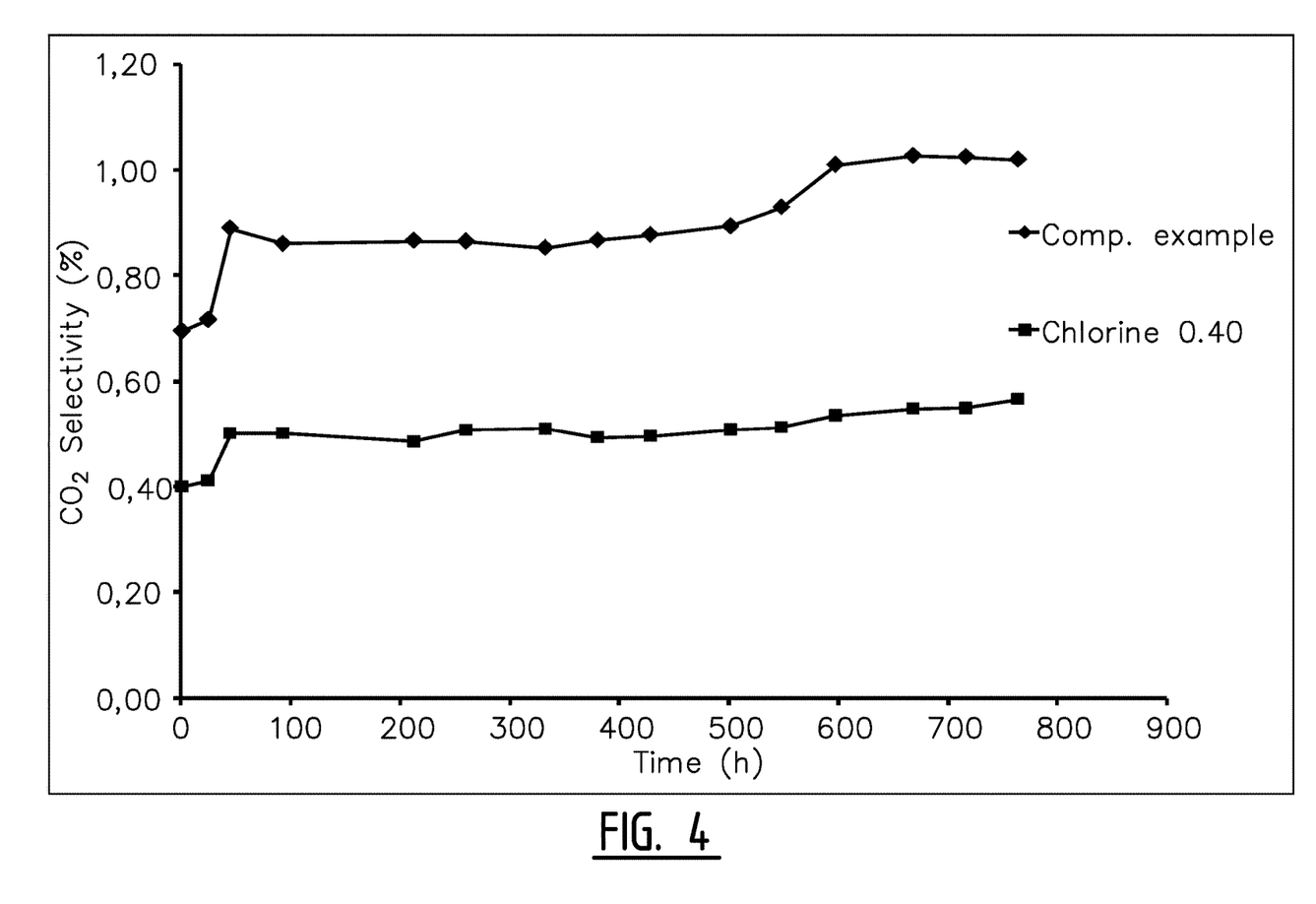
FIG. 4 is a graph of the CO2 selectivity factor against time.
Figure 6:
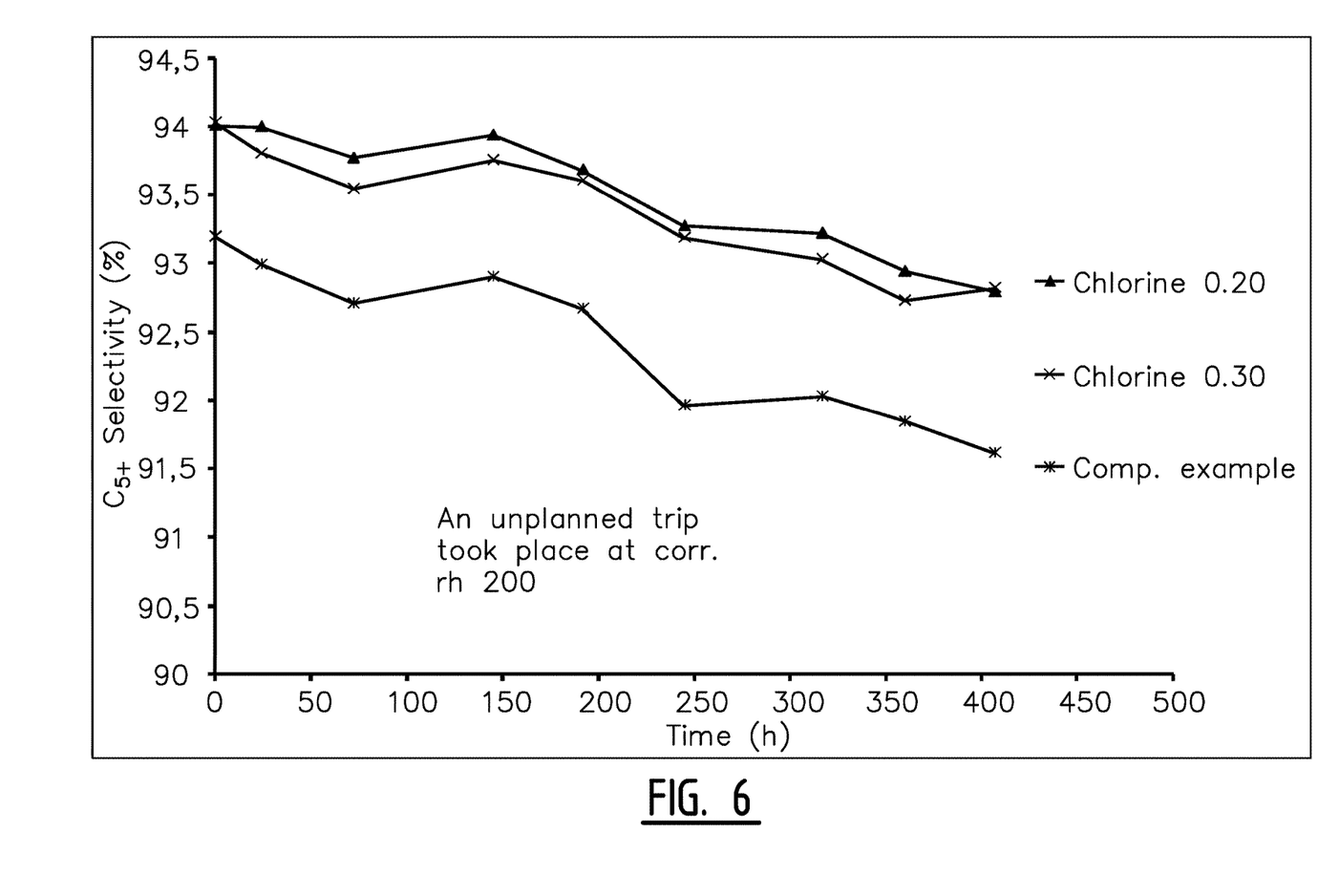
FIG. 6 is a graph of the CS+ selectivity factor against time.
Figure 7:
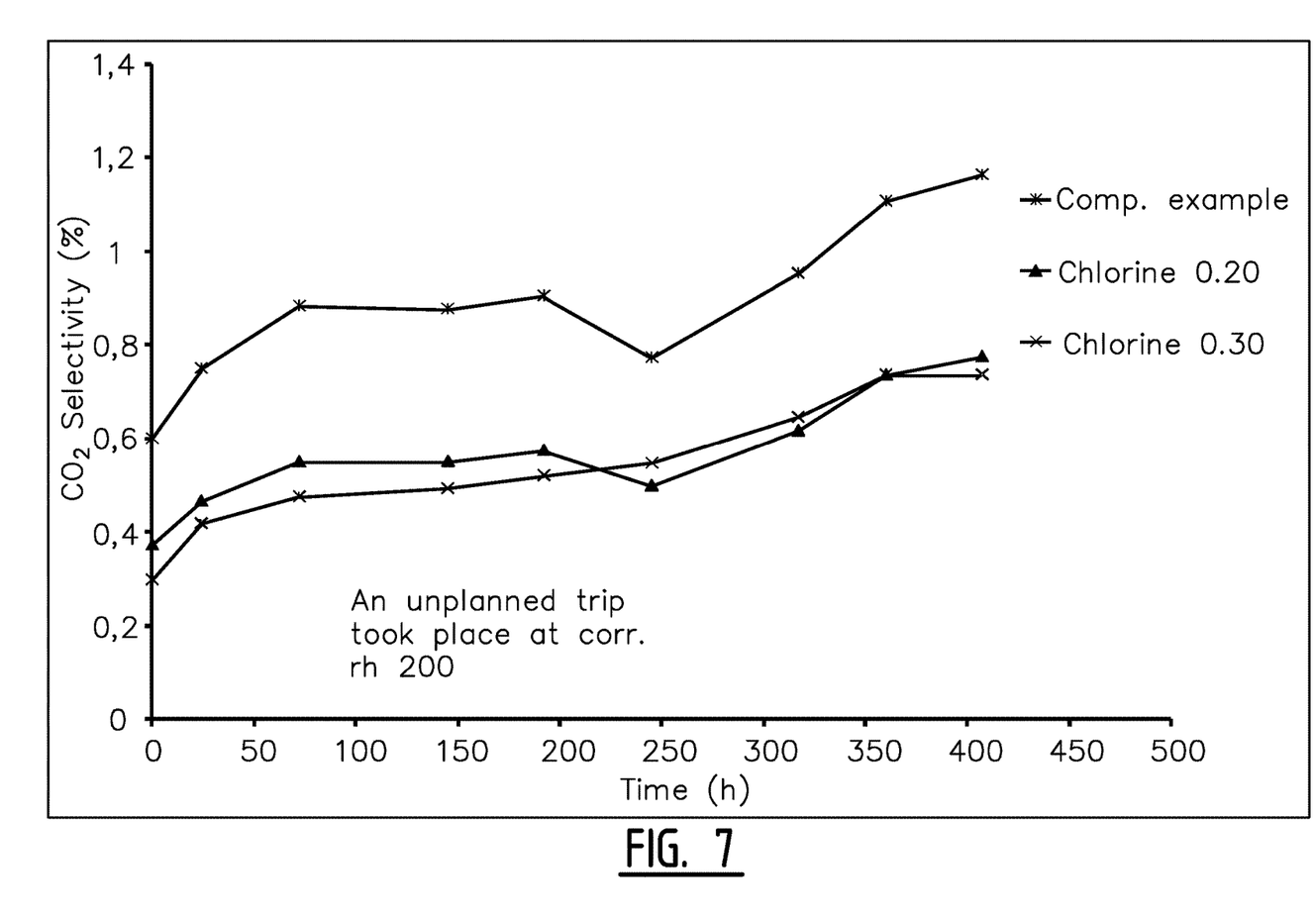
FIG. 7 is a graph of the CO2 selectivity factor against time.

FIGS. 3 and 4 show that the selectivity of Example 3 (0.4 wt % chlorine) towards $C_5+$ hydrocarbons is higher and the selectivity towards $CO_2$ is lower as compared to catalysts comprising 0.1 wt % chlorine. FIGS. 6 and 7 show that the selectivity of Examples 1 and 2 (0.2 and 0.3 wt % chlorine) towards $C_5+$ hydrocarbons is higher and the selectivity towards $CO_2$ is lower as compared to catalysts comprising 0.1 wt % chlorine.

FIGS. 5, 6 and 7 also show the stability of the different catalysts toward a high speed stop (trip) of the Fischer-Tropsch reaction. After the high speed stop at 200 run hours, the samples according to the invention showed a smaller decrease in activity and a smaller decrease in $C_5+$ hydrocarbons selectivity as compared to the Comparative Example.

Concluding, from Examples 1-4 is clear that the post-impregnation with cobalt chloride had a positive effect upon the activity during Fischer-Tropsch reaction, the stability, the selectivity towards C5+ hydrocarbons, and upon the ability to withstand a high-speed stop in the Fischer-Tropsch process.

Examples A1-A4

A base catalyst was prepared. The fixed bed catalyst particles of the base catalyst comprised 20 wt % cobalt and 1.1 wt % manganese on titania.

A part of the fixed bed particles of the base catalyst was impregnated with an aqueous cobalt chloride solution (CoCl2). During the impregnation 0.15 wt % of the element chlorine was added, calculated on the total weight of the dry catalyst. After the impregnation the catalyst particles were dried in air at 70° C. for 4 hours. In a subsequent final drying step in air, parts of the chorine impregnated catalyst particles were subjected to different final drying temperatures and times. After the final drying the chlorine content was determined by microcoulometry.

The catalyst particles were reduced with hydrogen at 280° C. for 18 hours, followed by a reduction with hydrogen at 290° C. for 2 hours.

The performance of each of the different samples prepared was tested using the following conditions in a Fischer-Tropsch reactor: a H2/CO ratio of 1.1, 25% N2, 60 bar, and 215° C. The selectivity of each of the samples was determined at 30% CO conversion after 70-90 hours time on stream. The base catalyst was used for a comparative example. Examples A1 to A4 are examples according to the present invention. The test results are summarized in Table 3.

TABLE 3

| Sample | Cl added (wt %) | Final drying step (° C./hours) | Cl content after drying (wt %) | Activity factor | C5+ select. (%) | CO2 select. (%) |
|---|---|---|---|---|---|---|
| Base catalyst | 0 | None | 0.07 | 1.37 | 89.3 | 2.8 |
| A1 | 0.15 | 120/1 | 0.23 | 1.55 | 90.5 | 1.8 |
| A2 | 0.15 | 200/1 | 0.22 | 1.48 | 90.5 | 1.8 |
| A3 | 0.15 | 300/1 | 0.21 | 1.44 | 90.9 | 1.8 |
| A4 | 0.15 | 300/24 | 0.13 | 1.33 | 89.8 | 2.1 |

From these experiments is clear that an increased amount of chlorine results in a higher selectivity towards C5+ hydrocarbons. The amount of chlorine can be adjusted by means of the drying temperature and the drying time.

Examples B1-B2

A base catalyst was prepared. The fixed bed catalyst particles of the base catalyst comprised 20 wt % cobalt and 1.1 wt % manganese on titania.

A part of the fixed bed particles of the base catalyst was impregnated with an aqueous cobalt chloride solution (CoCl2). During the impregnation 0.75 wt % of the element chlorine was added, calculated on the total weight of the dry catalyst. After the impregnation the catalyst particles were dried in air at 70° C. for 4 hours. In a subsequent final drying step in air, parts of the chorine impregnated catalyst particles were subjected to different final drying temperatures. After the final drying the chlorine content was determined by microcoulometry.

The performance was tested for the base catalyst and for a sample comprising 0.72 wt % chlorine after drying (sample B1). The samples were reduced with hydrogen at 280° C. for 18 hours, followed by a reduction with hydrogen at 290° C. for 2 hours.

The performance was tested using the following conditions in a Fischer-Tropsch reactor: a H2/CO ratio of 1.1, 25% N2, 60 bar, and 215° C. The selectivity was determined at 30% CO conversion after 70-90 hours time on stream. The base catalyst was used for a comparative example.

The test results are summarized in Table 4.

TABLE 4

| Sample | Cl added (wt %) | Final drying step (° C./hours) | Cl content after drying (wt %) | Activity factor | C5+ select. (%) | CO2 select. (%) |
|---|---|---|---|---|---|---|
| Base catalyst | 0 | None | 0.07 | 1.35 | 89.4 | 2.6 |

TABLE 4-continued

| Sample | Cl added (wt %) | Final drying step (° C./hours) | Cl content after drying (wt %) | Activity factor | C5+ select. (%) | CO2 select. (%) |
|---|---|---|---|---|---|---|
| B1 | 0.75 | 120/1 | 0.72 | 1.33 | 90.2 | 1.1 |
| B2 | 0.75 | 300/1 | 0.50 | | | |

From these experiments is clear that the addition of a small amount of chlorine results in a higher selectivity towards C5+ hydrocarbons. The activity of the catalysts measured in this series was comparable. The amount of chlorine can be adjusted by means of the drying temperature.

Examples C1-C3

A base catalyst was prepared. The fixed bed catalyst particles of the base catalyst comprised 20 wt % cobalt and 1.1 wt % manganese on titania.

A part of the fixed bed particles of the base catalyst was impregnated with an aqueous cobalt chloride solution (CoCl2). During the impregnation 3 wt % of the element chlorine was added, calculated on the total weight of the dry catalyst. After the impregnation the catalyst particles were dried in air at 70° C. for 4 hours. In a subsequent final drying step in air, parts of the chorine impregnated catalyst particles were subjected to different final drying temperatures. After the final drying the chlorine content was determined by microcoulometry.

The catalyst particles were reduced with hydrogen at 280° C. for 18 hours, followed by a reduction with hydrogen at 290° C. for 2 hours.

The performance of each of the different samples prepared was tested using the following conditions in a Fischer-Tropsch reactor: a H2/CO ratio of 1.11, 25% N2, 60 bar, and 215° C. The selectivity of each of the samples was determined at 30% CO conversion after 60-100 hours time on stream. The base catalyst was used for a comparative example. Examples C1 to C3 are examples according to the present invention. The test results are summarized in Table 5.

TABLE 5

| Sample | Cl added (wt %) | Final drying step (° C./hrs) | Cl content after drying (wt %) | Act. factor | C5+ select. (%) | CO2 select. (%) |
|---|---|---|---|---|---|---|
| Base cat. | 0 | None | 0.07 | 1.42 | 88.9 | 2.4 |
| C1 | 3 | 140/1 | 2.15 | 0.73 | 93.1 | 0.6 |
| C2 | 3 | 300/1 | 0.53 | 1.45 | 90.2 | 1.2 |
| C3 | 3 | 450/1 | 0.13 | | | |

From these experiments is clear that the addition of a small amount of chlorine results in a higher selectivity towards C5+ hydrocarbons. A relatively high amount of chlorine, 2.15 wt %, resulted in a relatively high selectivity towards C5+ hydrocarbons. The activity of this catalyst was relatively low, but the overall performance of this catalyst was fine due to the high selectivity towards C5+ hydrocarbons. The amount of chlorine can be adjusted by means of the drying temperature.

Examples D1-D2

A base catalyst was prepared. The fixed bed catalyst particles of the base catalyst comprised 20 wt % cobalt and 1.1 wt % manganese on titania.

A part of the fixed bed particles of the base catalyst was impregnated with an aqueous cobalt chloride solution (CoCl2). Another part of the fixed bed particles of the base catalyst was impregnated with an aqueous zinc chloride solution (ZnCl2). During the impregnation 0.15 wt % of the element chlorine was added, calculated on the total weight of the dry catalyst. After the impregnation the catalyst particles were dried in air at 120° C. for 1 hour. In a subsequent final drying step in air, the impregnated samples were dried at 300° C. for 1 hour.

The catalyst particles were reduced with hydrogen at 280° C. for 18 hours, followed by a reduction with hydrogen at 290° C. for 2 hours.

The performance of each of the different samples prepared was tested using the following conditions in a Fischer-Tropsch reactor: a H2/CO ratio of 1.1, 25% N2, 60 bar, and 215° C. The selectivity of each of the samples was determined at 30% CO conversion after 70-90 hours time on stream. Examples D1 and D2 are examples according to the present invention. The test results are summarized in Table 6.

TABLE 6

| Sample | Cl source | Final drying step (° C./hrs) | Activity factor | C5+ select. (%) | CO2 select. (%) |
|---|---|---|---|---|---|
| D1 | ZnCl2 | 300/1 | 1.43 | 90.0 | 1.9 |
| D2 | CoCl2 | 300/1 | 1.59 | 90.2 | 1.8 |

From these experiments is clear that the type of metal used to impregnate a metal salt of chloride is not important. The effects measured for the carbon C5+ selectivity is clearly due to the chloride which is impregnated, not to the cobalt. A very small amount of cobalt added to the 20 wt % cobalt comprising catalyst does not have a significant effect.

Examples E1-E2

A base catalyst was prepared. The fixed bed catalyst particles of the base catalyst comprised 20 wt % cobalt and 1.1 wt % manganese on titania.

A part of the fixed bed particles of the base catalyst was impregnated with an aqueous cobalt chloride solution (CoCl2). Another part of the fixed bed particles of the base catalyst was impregnated with an aqueous manganese chloride (MnCl2) solution. After the impregnation the catalyst particles were dried in air at about 75° C. for 4 hours. In a subsequent final drying step in air, both impregnated samples were dried at 300° C. for 1 hour.

After the final drying step, the chlorine content of each sample was determined.

The catalyst particles were reduced with hydrogen at 280° C. for 68 hours.

The performance of each of the different samples prepared was tested using the following conditions in a Fischer-Tropsch reactor: a H2/CO ratio of 1.1, 25% N2, 60 bar, and 215° C. The selectivity of each of the samples was determined at 30% CO conversion after 70-90 hours time on stream. The chlorine content in the base catalyst and in sample E1 was determined using coulometry, and the chlorine content in sample E2 was determined using XRF. Examples E1 and E2 are examples according to the present invention. The test results are summarized in Table 7.

TABLE 7

| Sample | Cl precursor | Final drying step (° C./hrs) | Cl content after drying (wt %) | Activity factor | C5+ select (%) | CO2 select (%) |
|---|---|---|---|---|---|---|
| Base catalyst | 0 | None | 0.07 | 1.61 | 89.8 | 2.1 |
| E1 | CoCl2 | 300/1 | 0.21 | 1.60 | 91.3 | 1.9 |
| E2 | MnCl2 | 300/1 | 0.25 | 1.40 | 90.0 | 1.7 |

From these experiments is clear that the type of metal used to impregnate a metal salt of chloride is not important. The effects measured for the carbon C5+ selectivity is clearly due to the chloride which is impregnated, not to the cobalt. A very small amount of cobalt added to the 20 wt % cobalt comprising catalyst does not have a significant effect.

Examples F1-F2

A base catalyst was prepared. The fixed bed catalyst particles of the base catalyst comprised 20 wt % cobalt and 1.1 wt % manganese on titania.

Parts of the fixed bed particles of the base catalyst were impregnated with different amounts of an aqueous cobalt chloride solution (CoCl2). After the impregnation the catalyst particles were dried in air at 120° C. for 2 hours. In a subsequent final drying step in air, both impregnated samples were dried at 290° C. for 1 hour.

After the final drying step, the chlorine content of each sample was determined.

The catalyst particles were reduced with hydrogen at 280° C. for 18 hours, followed by a reduction with hydrogen at 290° C. for 2 hours.

The performance of each of the different samples prepared was tested using the following conditions in a Fischer-Tropsch reactor: a H2/CO ratio of 1.12, 25% N2, 60 bar, and 215° C. The selectivity of each of the samples was determined at 30% CO conversion after 60-100 hours time on stream. Examples F1 and F2 are examples according to the present invention. The test results are summarized in Table 8.

TABLE 8

| Sample | Cl added (wt %) | Final drying step (° C./hrs) | Cl content after drying (wt %) | Activity factor | C5+ select. (%) | CO2 select. (%) |
|---|---|---|---|---|---|---|
| Base catalyst | 0 | None | 0.06 | 1.52 | 88.9 | 2.2 |
| F1 | 0.15 | 290/1 | 0.21 | 1.44 | 90.2 | 1.8 |
| F2 | 0.30 | 290/1 | 0.36 | 1.50 | 90.6 | 1.4 |

From these experiments is clear that an increased amount of chlorine results in a higher selectivity towards C5+ hydrocarbons. The amount of chlorine can be adjusted by means of the amount of chlorine that is impregnated on the particles.

Part II; Titania/Rhenium/Cobalt

Sample Preparation

Fixed bed particles were prepared as follows. Mixtures were prepared containing titania powder, cobalt hydroxide, a source of rhenium, water and several extrusion aids. The mixtures were kneaded. The mixtures were shaped using extrusion. The extrudates were dried and calcined. The obtained catalysts contained about 20 wt % cobalt and about 1 wt % of rhenium.

Example G1

A Re base catalyst was prepared. The fixed bed catalyst particles of the base catalyst comprised 20 wt % cobalt and 1.1 wt % rhenium on titania.

A part of the fixed bed particles of the base catalyst was impregnated with an aqueous cobalt chloride solution (CoCl2). After the impregnation the catalyst particles were dried in air at 140° C. for 1 hour. In a subsequent final drying step in air, the impregnated samples were dried at 300° C. for 1 hour.

The catalyst particles were reduced with hydrogen.

The performance of each of the different samples prepared was tested using the following conditions in a Fischer-Tropsch reactor: a H2/CO ratio of 1.1, 25% N2, 60 bar, and 215° C. The selectivity of each of the samples was determined at 30% CO conversion after 60-100 hours time on stream. Example G1 is an example according to the present invention. The test results are summarized in Table 9.

TABLE 9

| Sample | Cl added (wt %) | Final drying step (° C./hrs) | C5+ select. (%) | CO2 select. (%) |
|---|---|---|---|---|
| Re Base catalyst | 0 | None | 88.6 | 1.8 |
| G1 | 0.4 | 300/1 | 90.2 | 1.0 |

From these experiments is clear that the type of promoter in the catalyst is not important. The effect of chlorine on the C5+ selectivity and the CO2 selectivity are seen for Manganese (see above) as well as for Rhenium, see Re Base catalyst and Example G1 in Table 9.

Part III; Titania/Manganese/Cobalt—HCl

Sample Preparation

Fixed bed particles were prepared as follows. Mixtures were prepared containing titania powder, cobalt hydroxide, manganese hydroxide, water and several extrusion aids. The mixtures were kneaded. The mixtures were shaped using extrusion. The extrudates were dried at 80° C., and at this stage not calcined. The obtained catalysts contained about 20 wt % cobalt and about 1 wt % of manganese.

Example H1

A base catalyst was prepared. The fixed bed catalyst particles of the base catalyst comprised 20 wt % cobalt and 1.1 wt % manganese on titania.

Parts of the fixed bed particles of the base catalyst were calcined at 300° C. for 1 hour.

Parts of the fixed bed particles of the base catalyst were impregnated with an aqueous hydrochloric acid solution (HCl). After the impregnation the catalyst particles were dried in air at 60° C., followed by a final drying step in air at 300° C. for 1 hour.

The catalyst particles were reduced with hydrogen at 280° C. for 18 hours, followed by a reduction with hydrogen at 350° C. for 2 hours.

The performance of each of the different samples prepared was tested using the following conditions in a Fischer-Tropsch reactor: a H2/CO ratio of 1.1, 25% N2, 60 bar, and 215° C. The selectivity of each of the samples was determined at 30% CO conversion after 70-90 hours time on stream. Example H1 is an example according to the present invention. The test results are summarized in Table 10.

TABLE 10

| Sample | Cl added (wt %) | Activity factor | C5+ select. (%) | CO2 select. (%) |
|---|---|---|---|---|
| Base catalyst, dried at 300° C. | 0 | 1.38 | 91.7 | 1.7 |
| H1, impregnated with HCl, calcined at 300° C. | 0.2 | 1.39 | 93.9 | 1.2 |

From these experiments is clear that an increased amount of chlorine results in a higher selectivity towards C5+ hydrocarbons. This effect is thus seen for impregnation with metal chloride salts as well as for impregnation with HCl.

Part IV; Titania/Manganese/Cobalt—Nitrate Tests
Sample Preparation

Fixed bed particles were prepared as follows. Mixtures were prepared containing titania powder, cobalt hydroxide, manganese hydroxide, water and several extrusion aids. The mixtures were kneaded. The mixtures were shaped using extrusion. The extrudates were dried and calcined at about 595° C. The obtained catalysts contained about 20 wt % cobalt and about 1 wt % of manganese.

Example J1-J3

A base catalyst was prepared. The fixed bed catalyst particles of the base catalyst comprised 20 wt % cobalt and 1.1 wt % manganese on titania.

A part of the fixed bed particles of the base catalyst was impregnated with an aqueous hydrochloric acid solution (HCl) and dried at 80° C. for 1 hour, followed by calcination at 300° C. for 1 hour.

Another part of the fixed bed particles of the base catalyst was impregnated with an aqueous hydrochloric acid solution (HCl) and dried at 120° C. for 1 hour, followed by calcination at 300° C. for 1 hour.

Another part of the fixed bed particles of the base catalyst was impregnated with an aqueous nitric acid (HNO3) solution and and dried at 80° C. for 1 hour, followed by calcination at 300° C. for 1 hour.

After the final drying step, the chlorine content of each sample was determined by XRF.

The catalyst particles were reduced with hydrogen at 280° C. for 18 hours, followed by a reduction with hydrogen at 290° C. for 2 hours.

The performance of each of the different samples prepared was tested using the following conditions in a Fischer-Tropsch reactor: a H2/CO ratio of 1.1, 25% N2, 60 bar, and 215° C. The selectivity of each of the samples was determined at 30% CO conversion after 70-90 hours time on stream. Examples J2 and J3 are examples according to the present invention. The test results are summarized in Table 11.

TABLE 11

| Sample | Impregnated with | Cl content after drying (wt %) | Activity factor | C5+ select (%) | CO2 select (%) |
|---|---|---|---|---|---|
| Base catalyst | — | 0.07 | 1.39 | 89.5 | 2.4 |
| J1 | HNO3 | NA | 1.53 | 89.6 | 2.3 |
| J2 | HCl | 0.21 | 1.56 | 90.8 | 1.8 |
| J3 | HCl | 0.20 | 1.46 | 90.5 | 1.8 |

From these experiments is clear that nitric acid does not have the same effect as HCl. It is not the acidity that gives a positive effect on the C5+ selectivity, but the chlorine in HCl.

Similarly, impregnation with cobalt chloride had a positive effect on the C5+ selectivity, but impregnation with cobalt nitrate did not.

Part IV; Titania/Manganese/Cobalt—Organic Cl Compounds
Sample Preparation

Fixed bed particles were prepared as follows. Mixtures were prepared containing titania powder, cobalt hydroxide, manganese hydroxide, water and several extrusion aids. The mixtures were kneaded. The mixtures were shaped using extrusion. The extrudates were dried and calcined at about 595° C. The obtained catalysts contained about 20 wt % cobalt and about 1 wt % of manganese.

Example K1-K2

A base catalyst was prepared. The fixed bed catalyst particles of the base catalyst comprised 20 wt % cobalt and 1.1 wt % manganese on titania.

A part of the fixed bed particles of the base catalyst was impregnated with an aqueous tetra butyl ammonium chloride solution. Another part of the fixed bed particles of the base catalyst was impregnated with an aqueous propionic acid chloride solution. During the impregnation 0.15 wt % of the element chlorine was added, calculated on the total weight of the dry catalyst. After the impregnation the catalyst particles were dried in air at 80° C. for 1 hour. In a subsequent final drying step in air, the impregnated samples were dried at 300° C. for 1 hour.

After the final drying step, the chlorine content of each sample was determined by XRF.

The catalyst particles were reduced with hydrogen at 280° C. for 18 hours, followed by a reduction with hydrogen at 290° C. for 2 hours.

The performance of each of the different samples prepared was tested using the following conditions in a Fischer-Tropsch reactor: a H2/CO ratio of 1.1, 25% N2, 60 bar, and 215° C. The selectivity of each of the samples was determined at 30% CO conversion after 70-90 hours time on stream. Examples K1 and K2 are examples according to the present invention. The test results are summarized in Table 12.

TABLE 12

| Sample | Cl added (wt %) | Final drying step (° C./hrs) | Cl content after drying (wt %) | Activity factor | C5+ select. (%) | CO2 select. (%) |
|---|---|---|---|---|---|---|
| Base catalyst | 0 | None | 0.07 | 1.47 | 90.1 | 2.2 |
| K1, tetra butyl ammonium chloride | 0.15 | 300/1 | 0.18 | 1.38 | 91.1 | 1.9 |
| K2, propionic acid chloride | 0.15 | 300/1 | 0.21 | 1.50 | 91.0 | 1.8 |

From these experiments is clear that the source of chlorine is not important. An increased amount of chlorine results in a higher selectivity towards C5+ hydrocarbons. This effect is thus seen for impregnation with metal chloride salts, as well as for impregnation with HCl, as well as for impregnation with an organic chloride compound.

What is claimed is:
1. A process for performing a Fischer-Tropsch reaction comprising the following steps:

providing syngas to a reactor, said reactor comprising catalyst particles obtained by a process for preparing a chlorine comprising catalyst, comprising the following steps:
(a) providing a Fischer-Tropsch catalyst comprising:
titania
at least 5 weight percent cobalt, calculated on the total weight of the catalyst
in the range of between to 0.1 to 15 weight percent promoter calculated on the total weight of the catalyst, whereby the promoter comprises manganese, rhenium, Group 8-10 noble metals, or mixtures thereof;
(b) impregnating the catalyst with one or more solutions comprising cobalt salt of chloride until the catalyst comprises 0.13-10 weight percent of the element chlorine, calculated on the total weight of the catalyst;
(c) heating the impregnated catalyst at a temperature in the range of 100 to 350° C. for at least 5 minutes up to 2 days;
providing the following process conditions in the reactor:
a temperature in the range from 125 to 350° C., a pressure in the range from 5 to 150 bar absolute, and a gaseous hourly space velocity in the range from 500 to 10000 Nl/l/h;
removing Fischer-Tropsch product from the reactor.

2. A process according to claim 1, wherein the catalyst particles provided to said reactor are obtained by the steps (a)-(c), wherein the catalyst is impregnated in step (b) until the catalyst comprises 0.13-6, weight percent of the element chlorine, calculated on the total weight of the catalyst.

3. A process according to claim 1, wherein the Fischer-Tropsch catalyst that is provided in step (a) comprises in the range of between to 0.1 to 15 weight percent manganese, rhenium, Group 8-10 noble metals, or mixtures thereof calculated on the total weight of the catalyst.

4. A process according to claim 1, wherein the catalyst particles provided to said reactor are obtained by the steps (a)-(c), wherein the temperature and duration of the heating of step (c) are sufficient to effect the preparation of a catalyst comprising 0.13-3 weight percent of the element chlorine, calculated on the total weight of the catalyst.

5. A process according to claim 1, wherein the catalyst particles provided to said reactor are obtained by the steps (a)-(c), wherein the catalyst comprising titania, cobalt and a promoter which is provided in step (a) is a calcined catalyst that has been calcined at a temperature between 350 and 700° C. for at least 1 minute.

6. A process according to claim 5, wherein the catalyst particles provided to said reactor are obtained by the steps (a)-(c), wherein the one or more solutions comprising metal salt(s) of chloride with which the catalyst is impregnated in step (b) is/are a chloride of manganese, vanadium, titanium, silver, gold, zinc, platinum, palladium, zirconium, ruthenium, rhenium, rhodium, chromium, nickel, iron, osmium, or iridium or mixtures thereof.

7. A process according to claim 1, wherein the catalyst particles provided to said reactor are obtained by the steps (a)-(c), wherein the solution comprising chloride ions further comprises hydrochloric acid (HCl), one or more organic chloride compounds, or a combination thereof.

8. A process according to claim 1, wherein the catalyst particles provided to said reactor are obtained by the steps (a)-(c), wherein the catalyst provided in step (a) comprises catalyst particles which are fixed bed particle(s) larger than 1 mm, or immobilised slurry particles larger than 1 mm.

\* \* \* \* \*